(12) United States Patent
Griffith

(10) Patent No.: US 11,377,467 B2
(45) Date of Patent: Jul. 5, 2022

(54) CRYSTALLINE FORM OF GEMCITABINE

(71) Applicant: NuCana plc, Edinburgh (GB)

(72) Inventor: Hugh Griffith, Edinburgh (GB)

(73) Assignee: NuCana plc, Edinburgh (GB)

( * ) Notice: Subject to any disclaimer, the term of this patent is extended or adjusted under 35 U.S.C. 154(b) by 845 days.

(21) Appl. No.: 16/065,369

(22) PCT Filed: Dec. 21, 2016

(86) PCT No.: PCT/GB2016/054017
§ 371 (c)(1),
(2) Date: Jun. 22, 2018

(87) PCT Pub. No.: WO2017/109485
PCT Pub. Date: Jun. 29, 2017

(65) Prior Publication Data
US 2021/0188893 A1  Jun. 24, 2021

(30) Foreign Application Priority Data
Dec. 23, 2015  (GB) .................................. 1522771

(51) Int. Cl.
*C07H 19/06*  (2006.01)
(52) U.S. Cl.
CPC .......... *C07H 19/06* (2013.01); *C07B 2200/13* (2013.01)
(58) Field of Classification Search
None
See application file for complete search history.

(56) References Cited

U.S. PATENT DOCUMENTS

| | | | |
|---|---|---|---|
| 7,951,787 B2 | 5/2011 | McGuigan | |
| 8,907,106 B2 | 12/2014 | Coquerel et al. | |
| 9,834,577 B2 | 12/2017 | Dammalapati et al. | |
| 10,005,810 B2 | 6/2018 | McGuigan et al. | |
| 10,117,888 B2 | 11/2018 | Griffith et al. | |
| RE47,589 E | 9/2019 | McGuigan | |
| 2017/0107246 A1 | 4/2017 | Griffith et al. | |
| 2017/0226147 A1 | 8/2017 | Griffith | |
| 2018/0237466 A1* | 8/2018 | Yuan ........................ | C07F 9/24 |
| 2018/0244701 A1* | 8/2018 | Yuan ...................... | C07H 19/10 |
| 2018/0244710 A1 | 8/2018 | Yuan et al. | |
| 2018/0271889 A1 | 9/2018 | Griffith | |
| 2018/0273575 A1 | 9/2018 | McGuigan et al. | |
| 2018/0289733 A1 | 10/2018 | Griffith et al. | |
| 2018/0362571 A1 | 12/2018 | Kotala et al. | |
| 2019/0022117 A1 | 1/2019 | Griffith | |
| 2019/0022118 A1 | 1/2019 | Griffith et al. | |
| 2019/0381084 A1 | 12/2019 | Griffith | |

FOREIGN PATENT DOCUMENTS

| | | |
|---|---|---|
| FR | 2954310 | 6/2011 |
| WO | WO-2005/012327 A2 | 2/2005 |
| WO | WO-2014/076490 A1 | 5/2014 |
| WO | WO 2014/204856 A1 | 12/2014 |
| WO | WO 2015/081133 A2 | 6/2015 |
| WO | WO-2015/198058 A1 | 12/2015 |
| WO | WO-2015/198059 A1 | 12/2015 |
| WO | WO-2016/012781 A1 | 1/2016 |
| WO | WO-2016/055769 A1 | 4/2016 |
| WO | WO-2016/181093 A1 | 11/2016 |
| WO | WO-2017/060661 A1 | 4/2017 |
| WO | WO-2017/098252 A1 | 6/2017 |
| WO | WO-2017/109444 A1 | 6/2017 |
| WO | WO-2017/109485 A1 | 6/2017 |
| WO | WO-2017/109486 A1 | 6/2017 |
| WO | WO 2018/019188 A1 | 2/2018 |

OTHER PUBLICATIONS

International Search Report and Written Opinion for International Application No. PCT/GB2016/054017 dated May 2, 2017.
Caira, "Crystalline Polymorphism of Organic Compounds," Topics in Current Chemistry, 198:163-208 (1998).
Slusarczyk et al., "Application of ProTide Technology to Gemcitabine: A Successful Approach to Overcome the Key Cancer Resistance Mechanisms Leads to a New Agent (NUC-1031) in Clinical Development," Journal of Medicinal Chemsirty, 57(4):1531-1542 (2014).
U.S. Appl. No. 16/065,476, filed Griffith et al.
U.S. Appl. No. 16/065,598, Hellenthal et al.
International Search Report and Written Opinion for International Application No. PCT/G62004/003148 dated Jan. 20, 2005.
U.S. Appl. No. 15/279,611, McGuigan.
U.S. Pat. No. 9,321,798, B2, U.S. Appl. No. 13/877,673, McGuigan, Apr. 26, 2016.
U.S. Pat. No. 9,834,577, B2, U.S. Appl. No. 15/411,409, Dammalapati, Dec. 5, 2017.
U.S. Pat. No. 10,005,810, B2, U.S. Appl. No. 14/442,987, McGuigan et al., Jun. 26, 2018.
U.S. Pat. No. 10,117,888, B2, U.S. Appl. No. 15/308,475, Griffith et al., Nov. 6, 2018.
U.S. Pat. No. 10,660,912, B2, U.S. Appl. No. 15/753,237, Griffith et al., May 26, 2020.
U.S. Pat. No. 10,662,213, B2, U.S. Appl. No. 15/308,491, Griffith et al., May 26, 2020.
U.S. Pat. No. 10,669,300, B2, U.S. Appl. No. 15/514,673, Griffith et al., Jun. 2, 2020.
U.S. Pat. No. 10,774,104, B2, U.S. Appl. No. 16/060,681, Kotala et al., Sep. 15, 2020.
U.S. Pat. No. 10,786,523, B2, U.S. Appl. No. 16/142,948, Griffith et al., Sep. 29, 2020.
U.S. Pat. No. 11,040,051, B2, U.S. Appl. No. 17/010,338, Griffith et al., Jun. 22, 2021.
U.S. Pat. No. 11,040,997, B2, U.S. Appl. No. 15/994,378, McGuigan et al., Jun. 22, 2021.
US, 2019/0022117, A1, U.S. Appl. No. 16/065,498, Griffith et al., Jan. 24, 2019.

(Continued)

*Primary Examiner* — Layla D Berry
(74) *Attorney, Agent, or Firm* — Knowles Intellectual Property Strategies, LLC

(57) ABSTRACT

This invention relates to a crystalline form of gemcitabine-[phenyl-(benzoxy-L-alaninyl)]-(S)-phosphate.

5 Claims, 1 Drawing Sheet

(56) References Cited

OTHER PUBLICATIONS

US, 2019/0381084, A1, U.S. Appl. No. 16/065,476, Griffith et al., Dec. 19, 2019.
US, 2020/0197430, A1, U.S. Appl. No. 16/642,832, Griffith et al., Jun. 25, 2020.
US, 2020/0262861, A1, U.S. Appl. No. 16/865,527, Griffith et al., Aug. 20, 2020.
US, 2020/0268783, A1, U.S. Appl. No. 16/871,140, Griffith et al., Aug. 27, 2020.
US, 2021/0009625, A1, U.S. Appl. No. 16/991,765, Kotala et al., Jan. 14, 2021.
US, 2021/0100825, A1, U.S. Appl. No. 17/028,314, Griffith et al., Apr. 8, 2021.
US, U.S. Appl. No. 17/324,835, filed May 19, 2021, Griffith et al.
US, U.S. Appl. No. 17/323,367, filed May 18, 2021, McGuigan et al.
Blanka Gönczy; "Design, Synthesis and Biological Evaluation of Nucleotide Pro-drugs Centred on Clinically Active Anticancer Nucleosides," Thesis of Cardiff School of Pharmacy and Pharmaceutical Sciences Cardiff University; 2016.
Congiatu, Costantino; et al., "Design, Synthesis and Biological Evaluation of Some Novel Nucleotide Prodrugs as Potential Anticancer Agents," A Thesis submitted to the University of Wales for the Degree of Philosophiae Doctor, 2006; p. 1-290.
Darío, Braga, et al.; "Crystal Polymorphism and Multiple Crystal Forms", Springer-Verlag Berlin Heidelberg; Chapter in Structure and Bonding, 2009, RearchGate, pp. 25-50.
Gromova, B. V.; et al. Optical Rotatory Dispersion and Circular Dichroism of Mono- and Oligonucleotide-Amino Acides (Amidates), BioChimica ET Biophysica ACTA, 240(1971) 1-11.
Hilfker, Rolf; "Relevance of Solid-State Properties For Pharmaceutical Products", 2006, pp. 1-19.
McGuigan, et al.; "A phosphoramidate ProTide (NUC-1031) and acquired and intrinsic resistance to gemcitabine," ASCO University Meeting; XP-002750003; J Clin Oncol 29:2011; (suppl; abstr e13540); 2 pages.
Peterson, Matthew L.; et al.; "Expanding the Scope of Crystal Form Evaluation in Pharmaceutical Science", J Pharm Pharmaceut Sci. (www. cspsCanada.org) 9 (3): 317-326. (2006).

* cited by examiner

CRYSTALLINE FORM OF GEMCITABINE

RELATED APPLICATIONS

This application is a § 371 national stage application based on Patent Cooperation Treaty Application serial number PCT/GB2016/054017, filed Dec. 21, 2016; which claims the benefit of priority to United Kingdom Patent Application No. GB 1522771.3, filed Dec. 23, 2015.

This invention relates to a crystalline form of gemcitabine-[phenyl-benzoxy-L-alaninyl)]-(S)-phosphate.

BACKGROUND

Gemcitabine (1; marketed as Gemzar®) is an effective nucleoside analogue that is currently approved to treat breast, non-small cell lung, ovarian and pancreatic cancers and widely used to treat a variety of other cancers including bladder, biliary, colorectal and lymphoma.

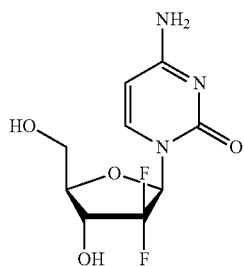

Gemcitabine's clinical utility is limited by a number of inherent and acquired resistance mechanisms. At the cellular level resistance is dependent on three parameters: (i) the down-regulation of deoxycytidine kinase, necessary for the activation into the phosphorylated moiety; (ii) the reduced expression of nucleoside transporters, in particular, hENT1 required for uptake by cancer cells; and (iii) the up-regulation of catalytic enzymes especially cytidine deaminase that degrades gemcitabine.

WO2005/012327 describes a series of nucleotide phosphate derivatives for gemcitabine and related nucleoside drug molecules. Among them gemcitabine-[phenyl-benzoxy-L-alaninyl)]-phosphate (NUC-1031; 2) is identified as a particularly effective compound. These derivatives appear to avoid many of the inherent and acquired resistance mechanisms which limit the utility of gemcitabine ('*Application of ProTide Technology to Gemcitabine: A Successful Approach to Overcome the Key Cancer Resistance Mechanisms Leads to a New Agent (NUC-1031) in Clinical Development*'; Slusarczyk et all; *J. Med. Chem.*; 2014, 57, 1531-1542).

ProGem1 was a first-time-in-human (FTIH), phase I, open label, two stage study to investigate the safety, tolerability, clinical efficacy, pharmacokinetics (PK) and pharmacodynamics (PD) of NUC-1031 given in two parallel dosing schedules in subjects with advanced solid malignancies (EudraCT Number: 2011-005232-26). Subjects had the following tumour types at study entry: colorectal cancer (7 subjects), unknown primary (3), ovarian cancer (12), breast cancer (4), pancreatic cancer (9), cholangiocarcinoma (7), endometrial cancer (3), cervical cancer (2), lung cancer (7), mesothelioma (3), oesophageal cancer (3), cancer of the fallopian tube (1), trophoblast (1), renal cancer (1), gastric cancer (1), anal cancer (1), cancer of the thymus (1) and osteosarcoma (1). The study confirmed NUC-1031's anti-tumour activity in patients with advanced progressive cancers, who have exhausted all standard therapeutic options, many of whom were resistant or refractory to prior nucleoside analogue therapy, including gemcitabine. Of particular note, the pharmacokinetic data showed that NUC-1031 as single agent generates around a 10-fold higher peak intracellular concentration ($C_{max}$) of the active triphosphate moiety (dFdCTP) than single agent gemcitabine at equimolar dose. Moreover, the intracellular exposure over time or Area Under the Curve (AUC) to dFdCTP, was 27-fold greater for NUC-1031 compared to historical data for gemcitabine from a number of published studies. Finally, the analyses revealed that NUC-1031 releases less than half the levels of the potentially toxic metabolite 2',2'-difluoro-2'-deoxyuridine (dFdU) normally associated with gemcitabine.

NUC-1031 2 is typically prepared as a mixture of two diastereoisomers, epimeric at the phosphate centre.

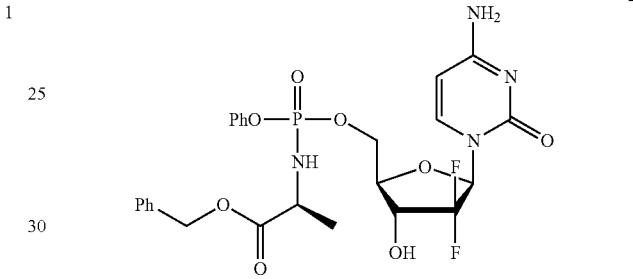

NUC-1031 2 is extremely lipophillic and thus poorly water soluble (by calculation: <0.1 mg/mL), and the ionisable moieties have calculated pKas which lie out-side the pH range suitable for parenteral administration. It has recently been discovered that the (S)-epimer 3 of gemcitabine-[phenyl-benzoxy-L-alaninyl)]phosphate has sufficient solubility in mixtures of a number of polar organic solvents with water to render it suitable for formulation and administration as a therapeutic agent. The solubility of the (R)-epimer (not shown) is considerably lower.

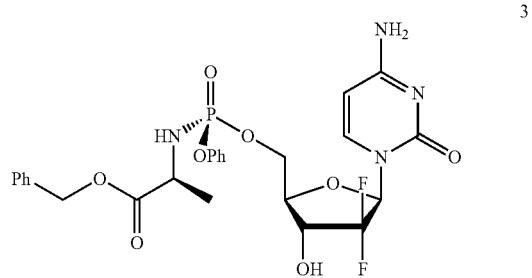

Both (S)- and (R)-epimers are therapeutically active but it appears preferable at the time of filing this application to administer gemcitabine-[phenyl-benzoxy-L-alaninyl)]-phosphate as the (S)-epimer.

It is an aim of certain embodiments of this invention to provide a stable crystalline form of gemcitabine-[phenyl-benzoxy-L-alaninyl)]-(S)-phosphate 3. It is an aim of certain embodiments of this invention to provide a crystalline form of gemcitabine-[phenyl-benzoxy-L-alaninyl)]-(S)-phosphate 3 that is more stable than other crystalline forms.

It is an aim of certain embodiments of this invention to provide a crystalline form of gemcitabine-[phenyl-benzoxy-L-alaninyl)]-(S)-phosphate 3 that is more soluble than other crystalline forms.

Certain embodiments of this invention satisfy some or all of the above aims.

BRIEF SUMMARY OF THE DISCLOSURE

The invention relates to a crystalline form of gemcitabine-[phenyl-benzoxy-L-alaninyl)]-(S)-phosphate, the crystalline form being form VIII.

Form VIII appeared physically stable upon stability stress testing. No change in crystalline form was observed upon storage under ambient light at 40° C. and 75% relative humidity for 7 days. Likewise, no decrease in purity was observed.

Said crystalline form (i.e. Form VIII) may be characterised in that said form has an XRPD pattern with at least two peaks (e.g. at least three peaks or with at least four peaks) at $2\theta$ selected from 4.9±0.2, 6.8±0.2, 9.1±0.2, 10.4±0.2, 20.3±0.2 and 21.0±0.2 when measured using Cu radiation with a $K_{\alpha 2}/K_{\alpha 1}$ ratio of 0.5. It may be that said crystalline form has an XRPD pattern with peaks at $2\theta$ 4.9±0.2, 6.8±0.2, 9.1±0.2, 10.4±0.2, 20.3±0.2 and 21.0±0.2 when measured using Cu radiation with a $K_{\alpha 2}/K_{\alpha 1}$ ratio of 0.5.

Said crystalline form (i.e. Form VIII) may be characterised in that said form has an XRPD pattern with at least two peaks (e.g. at least three peaks or with at least four peaks) at $2\theta$ selected from 4.9±0.1, 6.8±0.1, 9.1±0.1, 10.4±0.1, 20.3±0.1 and 21.0±0.1 when measured using Cu radiation with a $K_{\alpha 2}/K_{\alpha 1}$ ratio of 0.5. It may be that said crystalline form has an XRPD pattern with peaks at $2\theta$ 4.9±0.1, 6.8±0.1, 9.1±0.1, 10.4±0.1, 20.3±0.1 and 21.0±0.1 when measured using Cu radiation with a $K_{\alpha 2}/K_{\alpha 1}$ ratio of 0.5.

It may be that said crystalline form has an XRPD pattern substantially as shown in FIG. 1.

It may be that said crystalline form has an FTIR pattern, when measured as a suspension in Nujol, substantially as described in Example 3.

It may be that differential scanning calorimetry and/or thermogravimetric/differential thermal analysis of the crystal form shows an endotherm at 125.7±2.0° C. The endotherm may be at 125.7±1.0° C. The endotherm may be at 125.7±0.5° C.

The invention may also be as described in the following numbered clauses:
1. A crystalline form of gemcitabine-[phenyl-benzoxy-L-alaninyl)]-(S)-phosphate, the crystalline form being form VIII.
2. A crystalline form of clause 1, characterised in that said crystalline form has an XRPD pattern with at least two peaks at $2\theta$ selected from 4.9±0.2, 6.8±0.2, 9.1±0.2, 10.4±0.2, 20.3±0.2 and 21.0±0.2 when measured using Cu radiation with a $K_{\alpha 2}/K_{\alpha 1}$ ratio of 0.5.
3. A crystalline form of clause 2, characterised in that said crystalline form has an XRPD pattern with at least four peaks at $2\theta$ selected 4.9±0.2, 6.8±0.2, 9.1±0.2, 10.4±0.2, 20.3±0.2 and 21.0±0.2 when measured using Cu radiation with a $K_{\alpha 2}/K_{\alpha 1}$ ratio of 0.5.
4. A crystalline form of clause 3, characterised in that said crystalline form has an XRPD pattern with peaks at 4.9±0.2, 6.8±0.2, 9.1±0.2, 10.4±0.2, 20.3±0.2 and 21.0±0.2 when measured using Cu radiation with a $K_{\alpha 2}/K_{\alpha 1}$ ratio of 0.5.
5. A crystalline form of clause 1, characterised in that said crystalline form has an XRPD pattern substantially as shown in FIG. 1.
6. A crystalline form of any one of clauses 1 to 5, characterised in that said crystalline form has an FTIR pattern, when measured as a suspension in Nujol, substantially as described in Example 3.
7. A crystalline form of any one of clauses 1 to 6, characterised in that differential scanning calorimetry and/or thermogravimetric/differential thermal analysis of the crystal form shows an endotherm at 125.7±2.0° C.
8. A crystalline form of clause 7, characterised in that said endotherm is at 125.7±0.5° C.

BRIEF DESCRIPTION OF THE DRAWINGS

Embodiments of the invention are further described hereinafter with reference to the accompanying drawing, in which.

DETAILED DESCRIPTION

Figure 1:
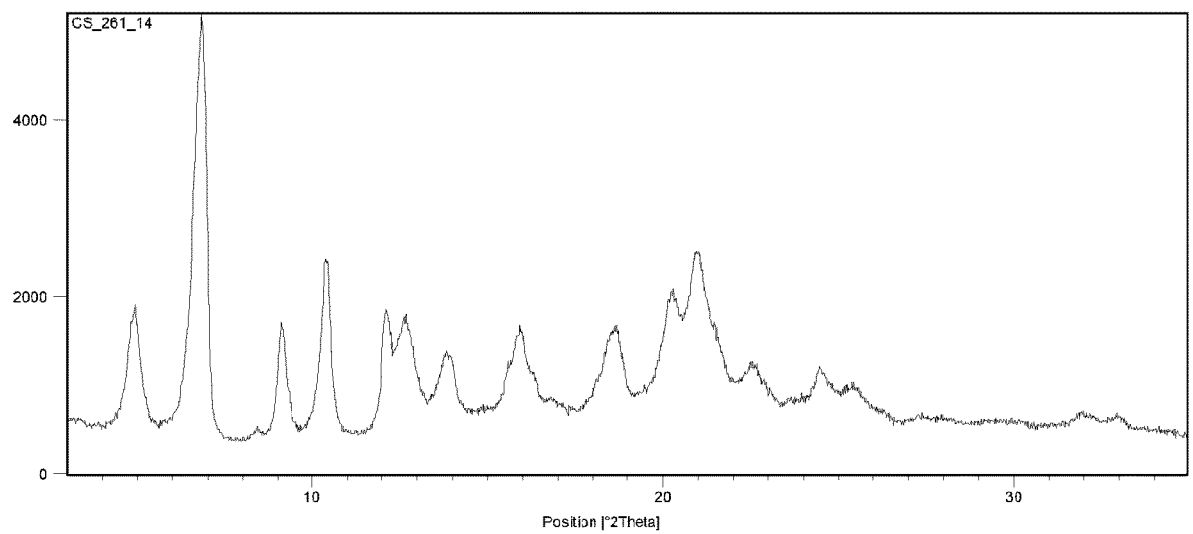
FIG. 1 is an XRPD spectrum of gemcitabine-[phenyl-benzoxy-L-alaninyl)]-(S)-phosphate crystalline form VIII.
Figure 2:
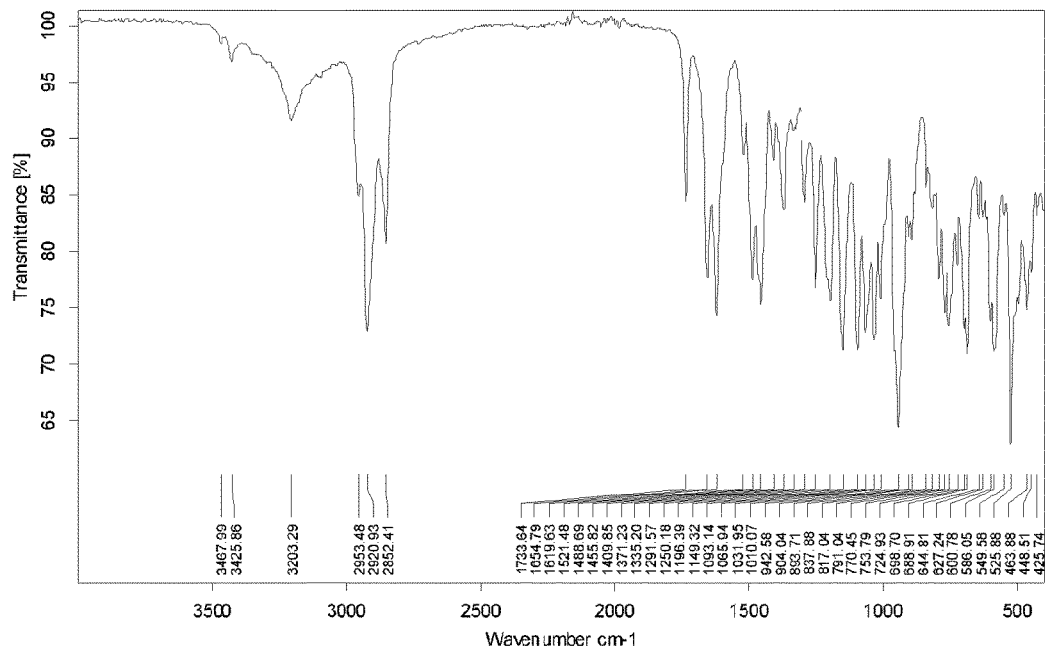
FIG. 2 is an FTIR spectrum of gemcitabine-[phenyl-benzoxy-L-alaninyl)]-(S)-phosphate crystalline form I, which corresponds to FIG. 2 in U.S. Pat. No. 10,669,300.

It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a power diffraction pattern substantially identical to those disclosed herein fall within the scope of the present disclosure (for further information see Jenkins, R & Snyder, R. L. 'Introduction to X-Ray Powder Diffractometry' John Wiley & Sons, 1996)."

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

Example 1—Process for the Isolation of (S)-Epimer in Form VIII

A mixture of the (R) and (S) isomers of 2'-Deoxy-2', 2'-difluoro-D-cytidine-5'-O-[phenyl (benzoxy-L-alaninyl)] phosphate (NUC-1031) was subjected to preparative HPLC under the following conditions:
  Column: X-Bridge Prep C18 (250×50) mm, 5 μm
  Mobile phase A: Milli-Q water
  Mobile Phase B: Methanol
  Flow rate: 80 mL/min
  Gradient (T/% B): 0/40, 5/40, 15/55. 31/55, 32/100, 36/100, 37/40, 40/40
  Detection: UV at 267 nm
  Sample Concentration: 57 mg/mL
  Injection Volume: c. 6 mL
  Load on column: c. 340 mg The first product to elute was the (R)-isomer (relative retention time (RRT) 0.97). The second product was the (S)-isomer (RRT 1.0). The fractions comprising substantially pure (S)-isomer were combined, the solvent was distilled off using a rotary evaporator at 40° C., the resultant solid was filtered, washed with water and dried under vacuum at 55-60° C. for 10 hours. The resultant solid was in crystalline Form VIII.

The individual isomers of gemcitabine-[phenyl-benzoxy-L-alaninyl)]-phosphate can be characterised using the following characterisation methods: Proton ($^1$H), carbon ($^{13}$C), phosphorus ($^{31}$P) and fluorine ($^{19}$F) NMR spectra were recorded on a Bruker Avance 500 spectrometer at 25° C. Spectra were auto-calibrated to the deuterated solvent peak and all $^{13}$C NMR and $^{31}$P NMR were proton-decoupled.

2'-Deoxy-2',2'-difluoro-D-cytidine-5'-O-[phenyl (benzyloxy-L-alaninyl)]-(S)-phosphate 3

(ES+) m/z, found: (M+Na$^+$) 603.14. $C_{25}H_{27}F_2N_4O_8$NaP required: (M$^+$) 580.47.

$^{31}$P NMR (202 MHz, MeOD): δ$_P$3.66

$^1$H NMR (500 MHz, MeOD): δ$_H$ 7.58 (d, J=7.5 Hz, 1H, H-6), 7.38-7.32 (m, 7H, ArH), 7.26-7.20 (m, 3H, ArH), 6.24 (t, J=7.5 Hz, 1H, H-1'), 5.84 (d, J=7.5 Hz, 1H, H-5), 5.20 (AB system, J$_{AB}$=12.0 Hz, 2H, OCH$_2$Ph), 4.46-4.43 (m, 1H, H-5'), 4.36-4.31 (m, 1H, H-5'), 4.25-4.19 (m, 1H, H-3'), 4.07-4.00 (m, 2H, H-4', CHCH$_3$), 1.38 (d, J=7.2 Hz, 3H, CHCH$_3$).

$^{19}$F NMR (470 MHz, MeOD): δ$_F$ –118.0 (d, J=241 Hz, F), –120.24 (broad d, J=241 Hz, F).

$^{13}$C NMR (125 MHz, MeOD): θ$_C$ 174.61 (d, $^3$J$_{C—P}$=5.0 Hz, C=O, ester), 167.63 (C—NH$_2$), 157.74 (C=O base), 152.10 (d, $^2$J$_{C—P}$=7.0 Hz, C—Ar), 142.40 (CH-base), 137.22 (C—Ar), 130.90, 129.63, 129.39, 129.32, 126.32 (CH—Ar), 124.51 (d, $^1$J$_{C—F}$=257 Hz, CF$_2$), 121.47, 121.43 (CH—Ar), 96.67 (CH-base), 85.92 (broad signal, C-1'), 80.31 (C-4'), 71.27 (apparent t, $^2$J$_{C—F}$=23.7 Hz, C-3'), 68.03 (OCH$_2$Ph), 65.73 (d, $^2$J$_{C—P}$=5.30 Hz, C-5'), 51.66 (CHCH$_3$), 20.42 (d, $^3$J$_{C—P}$=6.25 Hz, CHCH$_3$).

2'-deoxy-2',2'-difluoro-D-cytidine-5'-O-[phenyl(benzyloxy-L-alaninyl)]-(R)-phosphate (ES+) m/z, found: (M+Na$^+$) 603.14. $C_{25}H_{27}F_2N_4O_8$NaP required: (M$^+$) 580.47.

$^{31}$P NMR (202 MHz, MeOD): δ$_P$ 3.83

$^1$H NMR (500 MHz, MeOD): δ$_H$ 7.56 (d, J=7.5 Hz, 1H, H-6), 7.38-7.31 (m, 7H, ArH), 7.23-7.19 (m, 3H, ArH), 6.26 (t, J=7.5 Hz, 1H, H-1'), 5.88 (d, J=7.5 Hz, 1H, H-5), 5.20 (s, 2H, OCH$_2$Ph), 4.49-4.46 (m, 1H, H-5'), 4.38-4.34 (m, 1H, H-5'), 4.23-4.17 (m, 1H, H-3'), 4.07-4.01 (m, 2H, H-4', CHCH$_3$), 1.38 (d, J=7.2 Hz, 3H, CHCH$_3$).

$^{19}$F NMR (470 MHz, MeOD): δ$_F$ –118.3 (d, J=241 Hz, F), –120.38 (broad d, J=241 Hz, F).

$^{13}$C NMR (125 MHz, MeOD): δ$_C$ 174.65 (d, $^3$J$_{C—P}$=5.0 Hz, C=O, ester), 167.65 (C—NH$_2$), 157.75 (C=O base), 152.10 (d, $^2$J$_{C—P}$=7.0 Hz, C—Ar), 142.28 (CH-base), 137.50 (C—Ar), 130.86, 129.63, 129.40, 129.32, 126.31 (CH—Ar), 124.50 (d, $^1$J$_{C—F}$=257 Hz, CF$_2$), 121.44, 121.40 (CH—Ar), 96.67 (CH-base), 85.90 (broad signal, C-1'), 80.27 (C-4'), 71.30 (apparent t, $^2$J$_{C—F}$=23.7 Hz, C-3'), 68.02 (OCH$_2$Ph), 65.50 (C-5'), 51.83 (CHCH$_3$), 20.22 (d, $^3$J$_{C—P}$=7.5 Hz, CHCH$_3$).

Example 2—X-ray Powder Diffraction (XRPD)

A sample of the crystalline form VIII of (S) NUC-1031 was scanned between 3 and 35° 2θ. Material was gently compressed into a well mounted on Kapton film. The sample was then loaded into a PANalytical X'Pert Pro diffractometer running in transmission mode and analysed using the following experimental conditions:

| Raw Data Origin | XRD measurement (*.XRDML) |
| --- | --- |
| Start Position [°2θ] | 3.0066 |
| End Position [°2θ] | 34.9866 |
| Step Size [°2θ] | 0.0130 |
| Scan Step Time [s] | 67.9377 |
| Scan Type | Continuous |
| PSD Mode | Scanning |
| PSD Length [°2θ] | 3.35 |
| Offset [°2θ] | 0.0000 |
| Divergence Slit Type | Fixed |
| Divergence Slit Size [°] | 1.0000 |
| Specimen Length [mm] | 10.00 |
| Measurement Temperature [° C.] | 25.00 |
| Anode Material | Cu |
| K$_{α1}$ [Å] | 1.54060 |
| K$_{α2}$ [Å] | 1.54443 |
| K$_{α2}$/K$_{α1}$ Ratio | 0.50000 |
| Generator Settings | 40 mA, 40 kV |
| Goniometer Radius [mm] | 240.00 |
| Dist. Focus-Diverg. Slit [mm] | 91.00 |
| Incident Beam Monochromator | No |
| Spinning | No |

The resulting spectrum is shown in FIG. 1. The observed peaks were as follows:

| No. | Pos. [°2Th.] | d-spacing [Å] | Rel. Int. [%] |
|---|---|---|---|
| 1 | 4.9304 | 17.92351 | 21.88 |
| 2 | 6.8365 | 12.92989 | 100 |
| 3 | 9.1362 | 9.67976 | 20.06 |
| 4 | 10.3952 | 8.51013 | 43.26 |
| 5 | 12.1042 | 7.3121 | 22.73 |
| 6 | 12.6547 | 6.99523 | 20.96 |
| 7 | 13.8908 | 6.37541 | 21.17 |
| 8 | 15.9258 | 5.56504 | 18.86 |
| 9 | 18.6173 | 4.76614 | 27.09 |
| 10 | 20.2612 | 4.38299 | 25.71 |
| 11 | 20.9600 | 4.23843 | 44.37 |
| 12 | 22.5616 | 3.94104 | 12.48 |
| 13 | 24.4727 | 3.63744 | 11.95 |
| 14 | 25.4804 | 3.49583 | 8.13 |

2Th. = °2θ. Typically an error of ±0.2° 2θ is present in XRPD peak positions.

Example 3—Fourier Transform Infrared Spectroscopy (FTIR)

Infrared spectroscopy of the sample of crystalline form VIII of NUC-1031 was carried out on a Bruker ALPHA P spectrometer. A sample was measured as a suspension in Nujol (a paraffin oil), which has major peaks at 2950-2800 $cm^{-1}$, 1465-1450 $cm^{-1}$ and 1380-1370 $cm^{-1}$. Therefore, the recorded spectra showed these absorptions in addition to the material's absorption peaks. The suspensions were placed onto the centre of the plate of the spectrometer and the spectra were obtained using the following parameters:
Resolution: 4 $cm^{-1}$
Background Scan Time: 16 scans
Sample Scan Time: 16 scans
Data Collection: 4000 to 400 $cm^{-1}$
Result Spectrum: Transmittance
Software: OPUS version 6
The observed peaks were as follows:

| No. | Wavenumber [$cm^{-1}$] | Rel. Int. [%] | Width [$cm^{-1}$] |
|---|---|---|---|
| 1 | 460.6410 | 0.091 | 20.9976 |
| 2 | 524.0696 | 0.197 | 41.0650 |
| 3 | 583.0132 | 0.111 | 33.7248 |
| 4 | 600.0669 | 0.026 | 59.9923 |
| 5 | 690.1014 | 0.189 | 23.1044 |
| 6 | 736.2097 | 0.049 | 35.9004 |
| 7 | 773.5303 | 0.150 | 19.4015 |
| 8 | 818.2981 | 0.056 | 15.1795 |
| 9 | 938.4899 | 0.291 | 64.5837 |
| 10 | 958.7056 | 0.046 | 62.2171 |
| 11 | 1034.1569 | 0.136 | 54.2129 |
| 12 | 1065.3325 | 0.070 | 87.6196 |
| 13 | 1094.2451 | 0.200 | 26.0856 |
| 14 | 1147.0570 | 0.156 | 30.8392 |
| 15 | 1198.3714 | 0.154 | 32.9859 |
| 16 | 1250.5765 | 0.122 | 20.5444 |
| 17 | 1291.4533 | 0.086 | 266.7309 |
| *18* | *1372.1937* | *0.114* | *23.8828* |
| 19 | 1409.5966 | 0.045 | 11.4875 |
| 20 | 1456.7007 | 0.239 | 59.6082 |
| *21* | *1488.0228* | *0.086* | *217.5072* |
| 22 | 1521.7890 | 0.053 | 233.5179 |
| 23 | 1619.5707 | 0.280 | 62.2763 |
| 24 | 1654.2703 | 0.051 | 11.9171 |
| 25 | 1736.8756 | 0.139 | 22.7800 |
| *26* | *2852.5145* | *0.116* | *15.4965* |
| *27* | *2921.0059* | *0.412* | *78.3718* |
| 28 | 3203.9316 | 0.066 | 447.2671 |
| 29 | 3431.8837 | 0.022 | 38.3630 |
| 30 | 3457.7800 | 0.002 | 2185.7887 |

Peaks in italics correspond to those of Nujol (IR was collected as Nujol mull). The peaks at 1372.1937 $cm^{-1}$ and 1488.0228 $cm^{-1}$ appear to be an overlap of Nujol and Form VIII material.

Example 4—Thermogravimetric/Differential Thermal Analysis (TG/DTA)

Approximately 5 mg of material was weighed into an open aluminium pan and loaded into a simultaneous thermogravimetric/differential thermal analyser and equilibrated at room temperature. The sample was then heated at a rate of 10° C./min from 25° C. to 300° C. during which time the change in sample weight was recorded along with any differential thermal events. Nitrogen was used as the purge gas at a flow rate of 100 $cm^3$/min.

TG/DTA data for NUC-1031 S Form VIII showed a single slightly broad endotherm at onset 126.0° C., possibly associated with a melt. The material appeared dry by TG/DTA showing only 0.2% mass loss over the course of the endotherm. Sample decomposition was observed around 200° C.

Example 5—Differential Scanning Calorimetry (DSC)

Approximately 5 mg of material was weighed into an aluminium DSC pan and sealed non-hermetically with a pierced aluminium lid. The sample pan was loaded into a Seiko DSC6200 (equipped with a cooler). The sample and reference were heated up to 180° C. at a heating rate of 10° C./min.

DSC analysis of NUC-1031 S Form VIII was consistent with the TG/DTA analysis showing a single broad endotherm at onset 125.5° C. An initial broad endotherm was observed around 66° C.

I claim:

1. A crystalline form of gemcitabine-[phenyl-(benzoxy-L-alaninyl)]-(9-phosphate, wherein said crystalline form has an X-ray powder diffraction (XRPD) pattern with 2θ peaks at 4.9±0.2°, 6.8±0.2°, 9.1±0.2°, 10.4±0.2°, 20.3±0.2° and 21.0±0.2° when measured using Cu radiation with a $K_{\alpha 2}$/$K_{\alpha 1}$ ratio of 0.5.

2. The crystalline form of claim 1, wherein said crystalline form has an XRPD pattern substantially as shown in FIG. 1.

3. The crystalline form of claim 1, wherein said crystalline form has an FTIR pattern, when measured as a suspension in Nujol, substantially as shown in Example 3.

4. The crystalline form of claim 1, wherein differential scanning calorimetry or thermogravimetric/differential thermal analysis of the crystalline form shows an endotherm with an onset at 125.7±2.0° C.

5. The crystalline form of claim 4, wherein said endotherm has an onset at 125.7±0.5° C.

* * * * *